United States Patent [19]

Chaumont et al.

[11] Patent Number: 5,447,629
[45] Date of Patent: Sep. 5, 1995

[54] APPARATUS FOR PURIFYING A LIQUID EFFLUENT CONTAINING POLLUTANTS

[75] Inventors: Daniel Chaumont, Venelles; Catherine Thepenier, Mandsque; Claude Gudin, Aix en Provence, all of France

[73] Assignee: Commissariat a l'Energie Atomique, Paris, France

[21] Appl. No.: 153,971

[22] Filed: Nov. 18, 1993

[30] Foreign Application Priority Data

Nov. 23, 1992 [FR] France ................. 92 14037

[51] Int. Cl.⁶ ............. C02F 3/10; C02F 3/32
[52] U.S. Cl. ............. 210/96.1; 210/150; 210/177; 210/197; 210/205; 47/1.4; 435/286
[58] Field of Search ............. 47/1.4; 210/94, 96.1, 210/177, 197, 205, 602, 606, 610, 615, 616, 617, 150, 151; 435/314, 286

[56] References Cited

U.S. PATENT DOCUMENTS

| | | | |
|---|---|---|---|
| 3,926,807 | 12/1975 | Evers et al. | 210/177 |
| 4,503,150 | 3/1985 | Triolo | 435/41 |
| 4,676,956 | 6/1987 | Mori | 435/289 |
| 4,689,301 | 8/1987 | Adet et al. | 435/284 |
| 4,940,540 | 7/1990 | McDowell | 210/150 |
| 4,952,511 | 8/1990 | Radmer | 435/314 |
| 4,954,257 | 9/1990 | Vogelpohl et al. | 210/197 |
| 4,992,207 | 2/1991 | Darnall et al. | 210/616 |
| 5,108,929 | 4/1992 | Segura et al. | 210/96.1 |
| 5,151,347 | 9/1992 | Delente et al. | 435/289 |
| 5,179,012 | 1/1993 | Gudin et al. | 435/287 |
| 5,196,114 | 3/1993 | Burwell | 210/197 |
| 5,298,164 | 3/1994 | Hapach et al. | 210/615 |

FOREIGN PATENT DOCUMENTS

| | | | |
|---|---|---|---|
| 0112556 | 7/1984 | European Pat. Off. | |
| 0130116 | 1/1985 | European Pat. Off. | |
| 2162465 | 7/1973 | France | |
| 1513913 | 1/1988 | France | |
| WO91/07080 | 5/1991 | France | |
| 2357735 | 6/1974 | Germany | 210/602 |
| 2502515 | 11/1975 | Germany | 47/1.4 |
| 283093 | 3/1990 | Japan | 210/602 |
| 2154226 | 9/1985 | United Kingdom | 210/177 |

OTHER PUBLICATIONS

Patent Abstracts of Japan, vol. 9, No. 66 (C-271), Mar. 26, 1985, JP-A-59 199 099, Nov. 12, 1984.

*Primary Examiner*—Stanley S. Silverman
*Assistant Examiner*—Theodore M. Green
*Attorney, Agent, or Firm*—Oblon, Spivak, McClelland, Maier & Neustadt

[57] ABSTRACT

The invention relates to an apparatus for the purification of a liquid effluent containing pollutants, particularly metals and/or radionuclides, as well as to a process for purifying the effluent.

An object of the invention is to provide a continuously functioning purifying apparatus.

This object is achieved with the aid of an apparatus incorporating a confinement enclosure containing a support in which are immobilized living cells of photosynthetic microorganisms. The support is made from a material transparent to light rays. The apparatus also incorporates a mechanism for introducing and circulating the effluent to be treated and a culture medium within the enclosure.

13 Claims, 2 Drawing Sheets

5,447,629

APPARATUS FOR PURIFYING A LIQUID EFFLUENT CONTAINING POLLUTANTS

BACKGROUND OF THE INVENTION

1. Field of the Invention

The present invention relates to an apparatus for purifying a liquid effluent containing pollutants, particularly metals and/or radionuclides, as well as to a process for purifying said effluent.

2. Discussion of the Related Art

Numerous industrial processes lead to the formation of effluents containing metals such as e.g. copper or nickel, or heavy metals such as cadmium or mercury. Other processes lead to the formation of radionuclides such as uranium. All these substances constitute a significant pollution source and it is vital to treat them before discharging them into the natural medium.

The metals contained in a liquid effluent are either in the form of ions of the free metal, or are combined in numerous chemical forms. The ionic form of the free metal is generally the most toxic form, whereas the combined form is less toxic. It can even be considered that the toxicity of a metal element decreases with the degree of metal/organic material complexing. The metal is generally complexed with amino acids, polypeptides, fatty acids or polysaccharides. These compounds have the feature of being negatively charged and therefore constitute an anchoring site for metal ions, which are positively charged.

The prior art already discloses a number of processes making it possible to purify an effluent containing metals or radionuclides using bacteria or microalgae.

One of the processes consists of using biofilters, which are obscure reactors filled with rings, to which the bacteria are fixed. The function of these rings is to increase the surface and contact time between the bacteria fixed thereto and the effluent traversing the biofilter. These bacteria can trap certain pollutant elements, or can feed and develop therefrom.

However, if such a process type is not well controlled, it can lead to the replacement of a chemical contamination by a bacterial contamination, which can sometimes be just as dangerous. In addition, the affinity of the bacteria for these metals can lead to the destruction of their walls, so that their fixing properties are lost and they can die relatively rapidly.

Moreover, it has been demonstrated that microalgae are very powerful metal ion absorbers, particularly as a result of their large, negatively charged cellular surface. Certain species, such as e.g. *Porphyridium cruentum* produce and excrete large amounts of polysaccharides and they can represent up to 50% of the total quantity of organic materials produced by these microalgae. These polysaccharides are polyanionic and have $COO^-$ and $SO_3^-$ sites. This is precisely the characteristic which makes it possible to trap the heavy metals and radionuclides. This is a rapid, reversible phenomenon taking place in a few minutes.

The prior art already discloses a process for the purification of using microalgae and the so-called lagooning method, which consists of culturing in open air tanks a mixture of several microalgal species. The latter develop as a result of nutrient elements and in particular nitrogen supplied by the effluents to be treated. By a photosynthesis reaction, said microalgae produce oxygen, which is then used by the bacteria also located in the lagooning tank. This purification method is mixed, because it makes simultaneous use of the respective metabolisms of the algae and the bacteria, which makes it possible to purify pollutants of various types.

However, this open air procedure suffers from the disadvantage of not making it possible to control or check the selective development of a given microalgal species. It is therefore not possible to favor the specific extraction of a particular metal element or radionuclide.

The prior art also discloses a process industrially used by U.S. companies BIORECOVERY SYSTEM INC. and GEOMICROBIAL TECHNOLOGIES INC. for the accumulation of gold, mercury or uranium. In this procedure, dead cells of microalgae from the Chlorophyceae family (*Chlorella vulgaris* and *Chlorella regularis*) are trapped in an opaque substrate in the form of a silica gel column. The assembly constitutes a biofilter. The effluent to be treated passes through the silica gel column and the metal ions are fixed to the cellular walls of the microalgae by electrostatic forces. They occupy the negative sites of these walls, e.g. constituted by carboxylate ions, which are chelating agents. Therefore these microalgae can "bioaccumulate" up to 15% of their dry matter in uranium and up to 10% of their dry matter in gold. The pollutants are desorbed by modifying the pH of the medium containing the microalgae. Under the stress action caused by the pH modification, said microalgae release into the flow the heavy metals and radionuclides which can then be eluted.

According to the inventors of this procedure, it makes it possible to selectively trap certain heavy metals and not ions such as e.g. calcium, which often compete with these metals. Thus, this procedure has better performance characteristics than that using ion exchange resins.

However, this process still suffers from disadvantages. The biofilter can only be used a limited number of times. As the microalgal cells are dead, their walls can only trap a certain quantity of pollutants and when all the chelating agents have trapped a metal ion, it is necessary to recharge the biofilter with new microalgal cells. This leads to long and complex manipulations and a period of inactivity on the part of the biofilter.

An article published in the Compte rendu de l'academie des Sciences de Paris, Jul. 6 1981, series III, pp 35-37 entitled "Production of sulphated polysaccharides by a photobioreactor having immobilized *Porphyridium cruentum* cells", by C. GUDIN and D. THOMAS, discloses a photobioreactor making it possible to continuously culture living *Porphyridium cruentum* cells. This culturing takes place under artificial light in the presence of a constant $CO_2$ supply and in the absence of nitrogen. These cells continuously excrete a soluble sulphated capsular polysaccharide. However, this document provides no possibility for the treatment of a polluted effluent.

SUMMARY OF THE INVENTION

The present invention aims at obviating the disadvantages of the prior art effluent purifying apparatuses.

The invention therefore relates to an apparatus for the purification of a liquid effluent containing pollutants, particularly metals and/or radionuclides, incorporating a confinement enclosure (1) for receiving cells of photosynthetic microorganisms able to trap the pollutants, means (31) for introducing the effluent to be treated, means (35) for circulating said effluent through said enclosure (1), means (33, 65) for sampling the treated, liquid effluent and means (33) for sampling the pollutants, as well as means (23) for introducing $CO_2$ into the enclosure.

According to the features of the invention, the microorganism cells are living cells immobilized on a support (7), which at least partly occupies the interior of the enclosure (1) and is traversed by the effluent to be treated and the apparatus has means (21) for introducing and means (23) for circulating a liquid nutrient culture medium through the said support, the walls of the enclosure (1) and the support (7) of the cells being made from a material which is transparent to light rays.

Thus, unlike in the prior art purification apparatus (apparatuses of BIORECOVERY SYSTEM INC. and GEOMICROBIAL TECHNOLOGIES INC.), the microorganisms used here are living cells, which continually produce metabolites or chelating agents able to fix the polluting ions. Therefore the apparatus can be used permanently and makes it possible to carry out a continuous purification treatment without requiring periodic recharging of the support with microorganism cells. Therefore the operation of the apparatus is simplified. This support is chosen in such a way that it is easily traversed by the effluent to be treated and by the culture medium.

Advantageously the circulating means ensure the displacement of the effluent and the culture medium from bottom to top of the cell immobilization support, said support only extending over part of the total height of the confinement enclosure, so as to leave a lower free space and an upper free space within said enclosure. Moreover, a well forming an overflow is provided in the support in order to interconnect said two free spaces, the culture medium and the effluent flowing over into the well after passing into the upper free space.

This apparatus provides a circulation loop or circuit for the culture medium and effluent to be treated through the support. Therefore the effluent passes through the support by the necessary number of times until all the metals and radionuclides have been accumulated by the cells of the microorganisms.

Advantageously at least one tube is placed within the confinement cell and completely traverses the latter, said tube permitting the passage of the light rays from the outside. Preferably a lamp is located within the tube.

Thus, the microorganism culture is illuminated to the maximum, which makes it possible to completely perform the photosynthesis reaction and ensure good culturing and reproduction conditions for the microorganisms.

According to an advantageous feature of the invention, connected in series the apparatus comprises a sensor for measuring the pH within the confinement enclosure, a pH analyzer, a pH regulator and a valve acting on a $CO_2$ reservoir, so as to control the release of $CO_2$ into the enclosure.

By varying the $CO_2$ content in the culture medium, said apparatus also makes it possible to vary the pH of said medium. The increase in the $CO_2$ content and the decrease in the pH as a result of this causes stressing of the microorganism culture. The microorganism cells then release into the effluent and the liquid culture medium the pollutants which they have trapped. This gives a concentrated pollutant residue.

Finally, the invention also relates to a process for purifying a liquid effluent containing pollutants, particularly metals and/or radionuclides.

According to the features of the invention, said process comprises the stages of passing said effluent through a support in which are immobilized living cells of photosynthetic microorganisms able to trap said pollutants, after passing onto said support, the recovery of the treated liquid effluent obtained and acting in punctiform manner on the living cells of the microorganisms in order to force them to release into the circulating medium the trapped pollutants, so as to obtain a concentrated pollutant residue.

The procedure consisting of immobilizing the living cells within a support is particularly advantageous, because the pollutants are trapped in the walls or even within the living cells and are only eluted in the circulating liquid medium at certain periods, without the living cells being present in said liquid medium. It is consequently unnecessary to carry out a separation stage with respect to the solid and the liquid, which significantly simplifies the effluent purification process.

BRIEF DESCRIPTION OF THE DRAWINGS

The invention is described in greater detail hereinafter relative to a non-limitative embodiment and the attached drawings, wherein.

DESCRIPTION OF THE PREFERRED EMBODIMENTS

Figure 1:
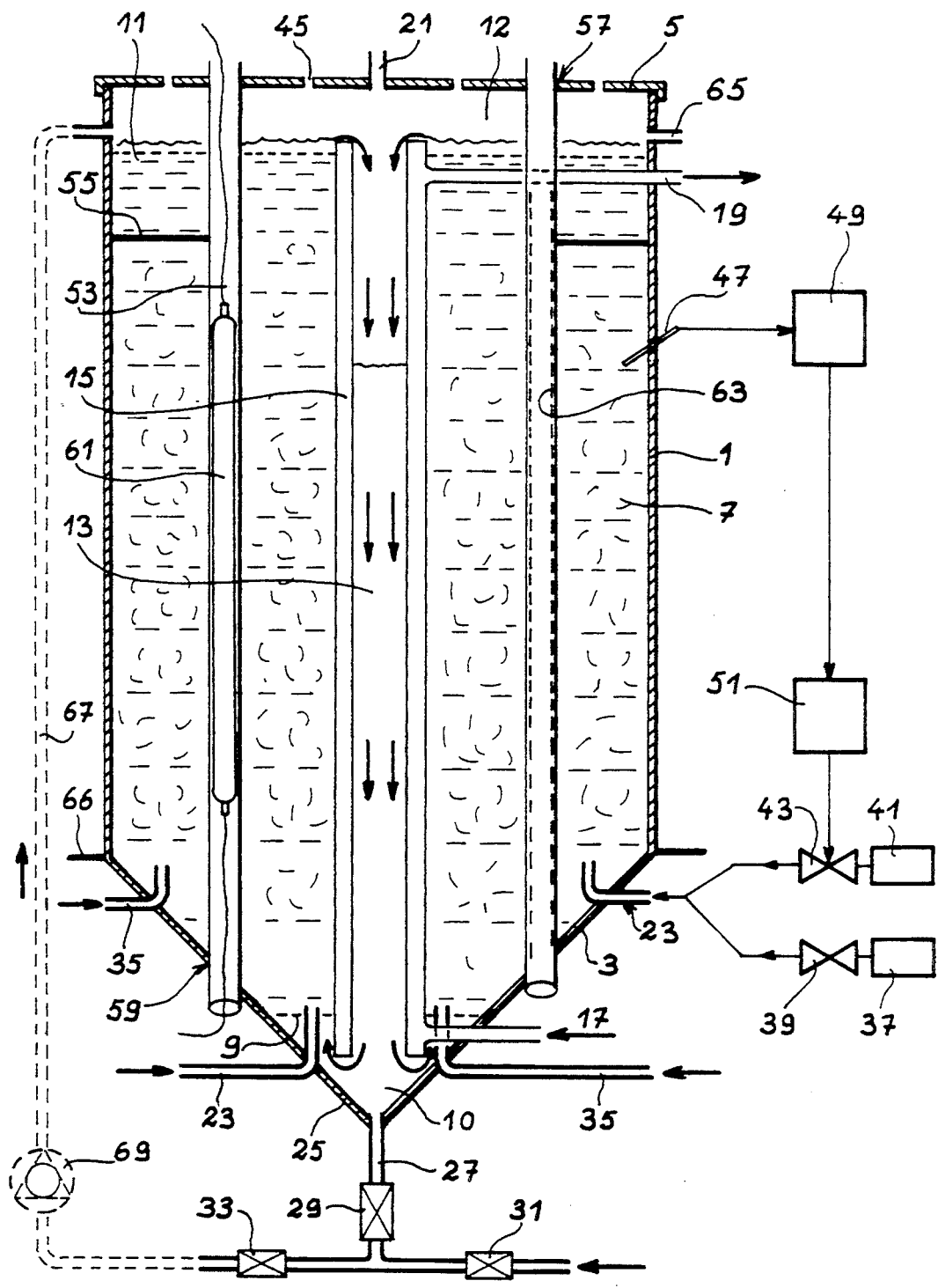
FIG. 1 is a sectional view of a liquid effluent purifying apparatus according to the invention.

The purifying apparatus according to the invention makes it possible to treat an effluent, more particularly containing metals (including heavy metals) and/or radionuclides. The apparatus according to the invention comprises a confinement enclosure 1 made from a material transparent to light rays. This material can e.g. be glass, polycarbonate, polymethacrylate or polyvinyl chloride (PVC). The light source placed around the confinement enclosure 1 can be of a natural or artificial nature. The enclosure 1 is substantially cylindrical. It is conical in its lower part 3 and its upper end is advantageously closed by a cover 5, which is also made from a material which is transparent to light. Although the cover 5 is not obligatory, it makes it possible to maintain a constant temperature within the enclosure and limit external pollution risks.

The enclosure 1 contains a support 7 within which are immobilized living cells of photosynthetic microorganisms. These living cells are chosen from among bacteria, microalgae or cells isolated from higher plants. For simplification purposes throughout the remainder of the description reference will only be made to microalgal cells.

The support 7 is advantageously made from a material which is transparent to light rays, e.g. polyurethane foam. Advantageously the support 7 is in the form of polyurethane foam fragments, preferably small fragments whose side dimensions are e.g. approximately 1.5 cm. This support is simultaneously traversed by the liquid effluent to be treated and by a liquid culture medium, as will be described hereinafter.

The fragmentation of the support makes it possible to obtain a grain size simultaneously offering a good compromise between the need of maintaining a good culture medium circulation, as will be described hereinafter, and the need to obtain a good diffusion of the effluent to be treated up to the microalgal cells immobilized in the support.

The immobilization of the living microalgal cells within the polyurethane foam can take place either by trapping the cells during the polymerization of a urethane prepolymer, or by colonizing the polyurethane foam from the outside by said microalgal cells. French patent 2 547 823 describes an example of a process for the preparation of a transparent wall made from polyurethane foam and in whose pores are distributed microorganisms. This process consists of introducing into a mold a mixture containing polyurethane foam precursors and a microorganism suspension, followed by the polymerization thereof.

The immobilization support 7 containing the living microalgal cells is kept in a defined space within the confinement enclosure 1 by means of a lower grid or grating 9 and an upper grid or grating 11. Moreover, within the confinement enclosure 1 and more specifically the support 7, there is a well 13 forming an overflow. Advantageously the well 13 is placed in the center of the confinement enclosure 1.

The upper grid 11 prevents support fragments 7 from dropping into the central well 13, while the lower grid 9 ensures a clear separation between the immobilization support 7 and the liquid medium flowing within the enclosure. Therefore the immobilization support 7 only extends over part of the total height of the confinement enclosure 1, so as to leave a free lower space 10 and a free upper space 12 within said enclosure. The central well 13 extends between these two free spaces and is advantageously vertical.

Preferably the walls 15 forming the well 13 are duplicated so as to permit the circulation between them of a heat regulating liquid. The latter is introduced into the bottom part of the well 13 by an inlet pipe 17 and passes out of it through an outlet pipe 19 located in the upper part of the well 13. This heat regulating liquid ensures that the liquid culture medium flowing within the confinement enclosure 1 is maintained at a constant temperature corresponding to the optimum culturing temperature for the microalgae.

This culture medium, which is indispensable to the development of the living microalgal cells, is introduced by means 21 constituted by a pipe passing through the cover 5 and which advantageously issues above the well 13. The purifying apparatus also has means 23 for circulating the culture medium within the enclosure and which can be constituted by a pump. However, another constructional variant of these means will be described hereinafter.

The conical end 25 of the lower part 3 of the confinement enclosure is provided with a T-shaped pipe 27. On the central part of said pipe 27 there is an inlet/outlet valve 29, while on one of the branches there is an inlet valve 31 for the effluent to be treated and on the other branch an outlet valve 33. The apparatus according to the invention also has means 35 for the circulation of the effluent to be treated and which can e.g. be constituted by a pump.

In practice, the means 23 for circulating the culture medium and the means 35 for circulating the effluent to be treated coincide, because the culture medium and the effluent mix within the enclosure. Advantageously said means 23 and 35 are constituted by at least one gas injector placed in the conical part 3 of the enclosure and making it possible to circulate the total liquid mass from bottom to top of the confinement enclosure and the support. The gaseous mixture introduced is constituted by air and advantageously $CO_2$. Preferably the mixture consists of 1 to 10% and preferably 2% $CO_2$. The introduced $CO_2$ aids photosynthesis. The air is stored in a reservoir 37 controlled by a valve 39 and the $CO_2$ in a reservoir 41 controlled by a motorized valve or electrovalve 43.

The gas bubbles rise through the immobilization support 7 and entrain the culture medium and effluent to be treated, which thus have a maximum contact with the living microalgal cells. Entrained in this way, the liquid medium reaches the top of the enclosure 1, namely the free upper space 12. This circulation principle is known as air lift. The cover 5 is also provided with orifices 45 permitting the degassing of the confinement enclosure.

As was briefly explained hereinbefore the polluting elements, i.e. the metals and radionuclides, trapped by the living microalgal cells immobilized in the support 7 can be desorbed under the action of a stress and in particular under the action of a pH shock or osmotic shock. The latter can be brought about by modifying the salinity of the liquid medium in which is immersed the immobilization support 7. A pH-meter 47 is placed in one of the side walls of the confinement enclosure 1 and is connected to a pH analyzer 49, which is itself connected to a pH regulator 51. As a function of a reference value, the pH can be regulated by the action of the electrovalve or motorized valve 43 connected to the pH regulator 51 on the one hand and to the carbon dioxide gas storage container 41 on the other. As described hereinbefore, this storage container or reservoir 41 issues by a pipe into the ejector 23, 35.

For simplification reasons in FIG. 1, only one pH regulating circuit is shown, but in fact all the injectors 23, 35 are connected to a regulating circuit or to at least one common regulating circuit. It is therefore possible either to optimize the photosynthesis of the microalgae by adjusting the pH and $CO_2$ to an optimum culturing value, or significantly lower said pH in order to exert a stress on the living cells and thus force them to desorb in the liquid medium the metals and other accumulated pollutants.

Apart from being advantageous, the confinement enclosure 1 can be equipped with at least one transparent tube 53 traversing it in a substantially vertical manner and there are preferably two tubes. Each tube 53 is fixed to the inner face of the walls of the confinement enclosure by a cross-piece 55. The cover 5 is also provided with an opening 57 to permit the passage of the tube 53 and for the same reasons the lower part 3 of the enclosure has an opening 59. These tubes 53 are open at both ends. They serve to favour the penetration of natural light into the confinement enclosure 1 or for receiving an artificial light source such as an optical fiber or a fluorescent tube 61, as is shown in the left-hand part of FIG. 1. The fact that each end of each tube 53 is open makes it possible to improve the thermal control of the enclosure 1 and evacuate by convection a large quantity of calories e.g. supplied by an artificial light source.

Advantageously the inner wall of these transparent tubes 53 can be covered with a selective film 63 favoring the predominance of certain wavelengths. This film 63 is partly shown on the right-hand tube 53 in FIG. 1. Consequently each of these transparent tubes 53 makes it possible to modify the duration of the photoperiod, the light quantity received and the spectral quality of said light. The confinement enclosure 1 is also provided with at least one pour-over pipe 65 located in the upper free space 12 of the enclosure and which is therefore flush with the liquid medium level and constitutes an overflow.

Finally, it should be noted that the enclosure 1 is provided at its bottom with an annular support 66 so that it can be kept vertical.

The operation of this purifying apparatus will now be described in greater detail.

The living microalgal cells are trapped within the polyurethane foam, as stated hereinbefore, and the foam fragments are introduced into the confinement enclosure. The nitrogen-enriched liquid culture medium is also introduced into the enclosure by the pipe 21, so that the culture can grow and multiply, $CO_2$ also being added.

In the presence of light and $CO_2$, the microalgae perform a photosynthesis reaction during which they transform the carbon dioxide gas into oxygen and form biomass. This biochemical reaction corresponds to a photopolymerization of the carbon dioxide gas and can be represented by the following MYERS equation:

$$6.14\ CO_2 + 3.65\ H_2O + NH_3 \rightarrow C_{6.14}H_{10.3}O_{2.2} + 6.85\ O_2.$$

The oxygen produced can optionally be recovered for use in other applications. The use of light-transparent polyurethane foam consequently makes it possible to culture the microalgae under conditions which are photo-autotrophic with respect to $CO_2$.

The choice of the microalgal species to be immobilized is largely dependent on the nature of the effluent to be purified. However, in a preferred embodiment of the invention, they are microalgae of the species *Porphyridium cruentum*. The microalgae of this species are able to produce exocellular polysaccharides.

The following table 1 gives a few examples of microalgae which can be cultured within the purifying apparatus according to the invention, as a function of the metals or radionuclides contained in the effluent which it is desired to treat.

TABLE 1

| Microalgal species | Elements which can be trapped by said microalgal species |
|---|---|
| *Chlorella vulgaris* | copper, gold |
| Chlorella sp | mercury, uranium |
| *Chlorella regularis* | manganese, molybdenum, uranium |
| Scenedesmus | cadmium, molybdenum, uranium |
| Euglena sp | iron, aluminum, barium, zinc, manganese, nickel, copper, lead, uranium, thorium |

Obviously the above list is not exhaustive and it is possible to culture other microalgal species within the apparatus according to the invention. In the case of species producing polysaccharides such as the *Porphyridium cruentum* used here and when the microalgal cells have reached an adequate development stage to colonize most of the immobilization supports 7, the nitrogen supply is removed or greatly reduced. The microalgae then react and protect themselves by synthesizing an exocellular polysaccharide, which remains partly attached to the outer surface of the cell and whereof the other part is hydrosolubilized in the liquid medium surrounding the supports 7. These polysaccharides fix the metal ions or radionuclides.

Other species of microalgae such as Chlorella or Scenedesmus can be cultured in the biofilter in the presence of nitrogen. In this case, the microalgae produce few or very few polysaccharides and the polluting elements are accumulated within the algal cell.

The method of concentrating the metals or radionuclides is dependent on the cultured algal species and the way in which the concentrated elements are recovered and the operating procedure of the biofilter are also dependent on said species.

In the case of an algal strain such as *Porpyridium cruentum* producing an exocellular polysaccharide, storage takes place outside the cell. In this case, the biofilter is filled with the effluent to be purified by means of valves 29 and 31 and said effluent circulates in the biofilter. As described hereinbefore, the ions considered to be polluting (heavy metals, radionuclides, etc.) fix to the polysaccharide, thus forming an electrically neutral complex. An effluent no longer containing any or virtually any pollutant in ionic form is considered to be purified, i.e. an effluent whereof all the ions have been fixed to the polysaccharide. The depollution state can be checked by precipitating the polysaccharide and therefore with it the fixed polluting ions, e.g. by adding alcohol to an effluent sample. The dosing of the polluting ion into the supernatant product following precipitation then makes it possible to determine, compared with the quantity initially present in the effluent, what is the proportion of ions fixed to the polysaccharide and therefore the degree of purification of said effluent. If the proportion of residual ions in the effluent is zero or very low, said effluent is eluted by valves 29 and 33. The thus recovered effluent is treated with an alcohol, e.g. in order to bring about precipitation of the hydrosolubilized exocellular polysaccharides and thus recover the polluting elements, such as metals and radionuclides.

In the case of a strain such as Chlorella, where the storage of the element to be eliminated is intracellular, the operating procdure is slightly different. The biofilter is filled by the valves 29 and 31 with the effluent to be purified. At the end of a time sufficient for the complete purification of the effluent, the treated liquid effluent obtained is eluted by means of the valves 29 and 33. These biofilter filling and eluting operations are repeated several times. The effluent is eluted and the biofilter is again filled as soon as the metal or radionuclide concentration of the effluent to be treated is zero and this takes place until the microalgae are saturated (maximum intracellular concentration). This saturation occurs when the concentration of the effluent in chemical elements to be eliminated no longer decreases.

At this time, under the action of a pH shock or a modification of the osmotic pressure, or other physicochemical parameters, the concentrated polluting elements in the algal cell are excreted into the liquid medium surrounding the immobilization support 7. The biofilter is then eluted for the last time by the valves 29 and 33 and the liquid obtained corresponds to a concentrate of the chemical elements to be eliminated. The concentration factor obtained will be a function of the number of filling and eluting operations which have had to be carried out.

The two operating procedures described hereinbefore are batchwise or semicontinuous, i.e. the effluent is charged and removed only when all the polluting elements have been eliminated from the effluent.

It is possible to use a continuous operating procedure and then a random algal species can be chosen. In this case, the biofilter is filled on the first occasion with the effluent by means of the valves 29 and 31, but instead of being periodically emptied and then recharged, said effluent is then continuously supplied using a micropump via an orifice. It is the delivery of said micropump which governs the diluting rate and the average residence time of said effluent in the biofilter and therefore the degree of purification of the effluent. A quantity of liquid equivalent to that introduced is drawn off by the pour-over pipe 65 or with the aid of a second micropump. It should be noted that the position of the pipe 21 in the center of the cover 5 is appropriate, because it avoids the supplied effluent from possibly being immediately drawn off by the pipe 65.

In the case of an intracellular storage, the effluent obtained in this way is considered to be purified. When the polluting element concentration increases in the liquid medium contained in the biofilter, the algae are "saturated" with said element. The latter is then recovered as described hereinbefore by a pH or osmotic shock.

In the case of an extracellular storage on a polysaccharide, the recovered effluent is treated with alcohol, e.g. as described hereinbefore. It is then possible to supply at the same time as the effluent, certain nutrient elements aiding the synthesis of the polysaccharides. The production of these polysaccharides is then constant in time, so that a continuous operating procedure can be maintained for long periods.

Moreover, in the case of the absence of aeration or a too viscous culture medium, it is possible to recycle the effluent to be treated by sampling it at the outlet valve 33 and introducing it again into the confinement enclosure, namely into the upper free space 12, by a recirculating pipe 67, which is equipped with a pump 69. This optional variant is illustrated in mixed line form in FIG. 1.

Figure 2:
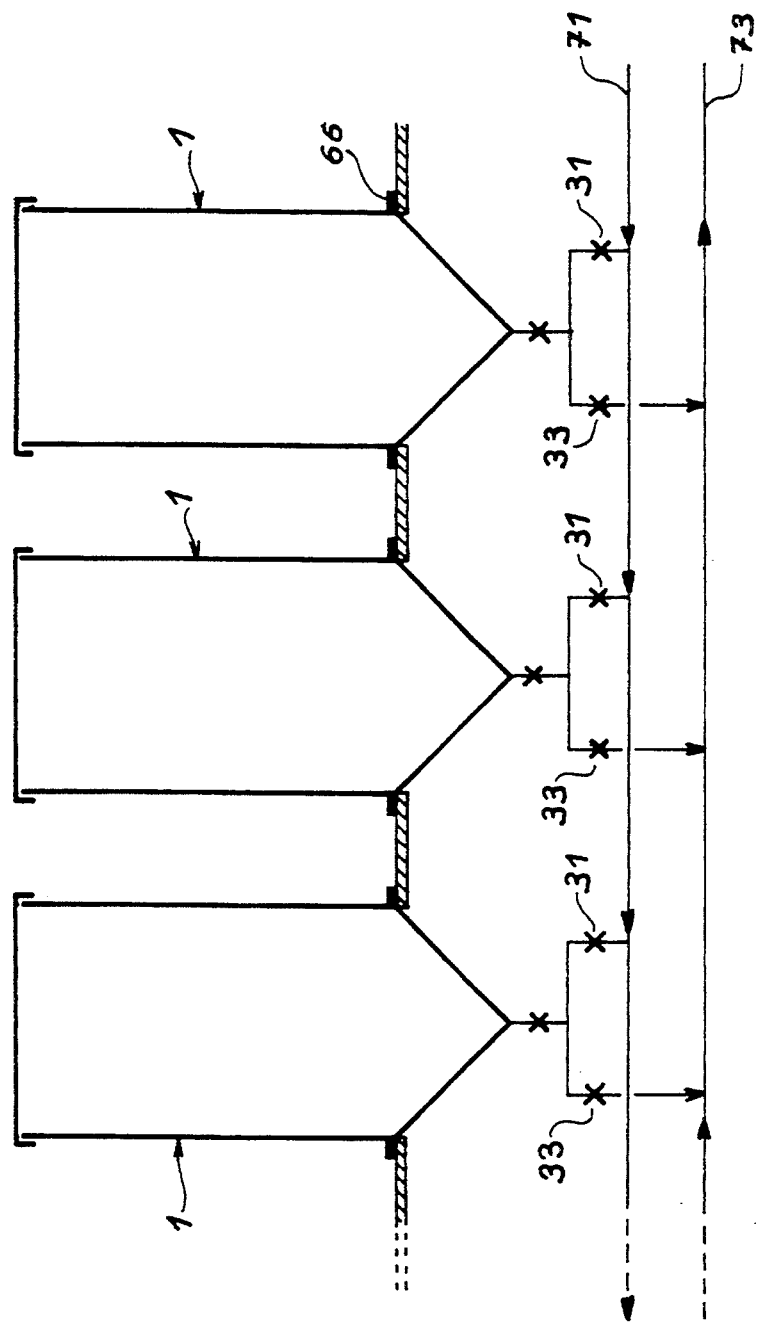
FIG. 2 is a diagram illustrating an overall purification system in which several purifying apparatuses according to the invention are connected in parallel.

Finally, as illustrated in FIG. 2, several purifying apparatuses according to the invention can be connected in parallel. All the inlet valves 31 are fitted to a common inlet pipe 71 and all the outlet valves 33 to a common outlet pipe 73.

We claim:

1. An apparatus for the purification of liquid effluent containing pollutants, particularly metals and/or radionuclides, the apparatus comprising:

a confinement enclosure for receiving cells of microorganisms able to trap the pollutants;

means for introducing the effluent to be treated into said enclosure;

means for circulating said effluent through said enclosure; and means for sampling the treated, liquid effluent and means for sampling the pollutants;

wherein:

the micro-organism cells are living photosynthetic cells immobilized on a support which at least partly occupies an interior of the enclosure and is traversed by the effluent to be treated, the enclosure comprising walls such that the walls of the enclosure and the support of the cells are made from a material which is transparent to light rays;

the apparatus further comprising:

means for introducing $CO_2$ into the enclosure;

means for introducing and means for circulating a liquid nutrient culture medium through said support, the circulating means for the effluent and the circulating means for the culture medium incorporating an injector connected to an air reservoir and to a $CO_2$ reservoir and permitting an injection of air bubbles containing $CO_2$ into a lower part of the enclosure; and connected in series, a sensor for measuring a pH within a confinement enclosure, a pH analyzer, a pH regulator and a valve acting on the $CO_2$ reservoir, so as to control a release of $CO_2$ within said enclosure.

2. A purifying apparatus according to claim 1, wherein the circulating means for the culture medium and the circulating means of the effluent ensure a displacement of the effluent and the culture medium from a bottom to a top of the support, said support only extends over part of a total height of the enclosure, so as to provide a free lower space and a free upper space within said enclosure, and a well forming an overflow is provided in the support for interconnecting said two free spaces, the culture medium and the effluent overflowing into said well after reaching the upper free space.

3. A purifying apparatus according to claim 2, wherein the well comprises walls, such that the walls of the well are duplicated, so that a circulation of a thermal regulation fluid is possible between the same.

4. A purifying apparatus according to claim 2, wherein at least one tube is placed within the confinement enclosure and completely traverses the enclosure, said tube permitting a passage of light rays from outside the enclosure.

5. A purifying apparatus according to claim 4, wherein a lamp is placed within said tube.

6. A purifying apparatus according to claim 4, wherein a film which makes it possible to select a passage of predetermined wavelengths covers inner walls of the tube.

7. A purifying apparatus according to claim 4, wherein the well forming an overflow is placed in a center of the confinement enclosure, and at least two tubes are uniformly distributed around it.

8. A purifying apparatus according to claim 2, wherein the sampling means for the liquid effluent are connected by a pipe equipped with a pump to the upper free space of the confinement enclosure.

9. A purifying apparatus according to claim 1, wherein the injector connected to the $CO_2$ reservoir permits the injection of air containing 1 to 10% $CO_2$.

10. A purifying apparatus according to claim 1, wherein the treated liquid effluent sampling means comprise a pour-over pipe at a top of the confinement enclosure.

11. A purifying apparatus according to claim 1, wherein the support comprises polyurethane foam fragments.

12. A purifying apparatus according to claim 1, wherein the photosynthetic microorganism is a microalgal species, a bacteria or a cell isolated from higher plants.

13. A purifying apparatus according to claim 12, wherein the microalgal species is *Porphyridium cruentum* and produces an exocellular polysaccharide.

* * * * *